United States Patent [19]
Marotta et al.

[11] Patent Number: 5,990,380
[45] Date of Patent: Nov. 23, 1999

[54] PERCUTANEOUS BIOFIXED MEDICAL IMPLANTS

[75] Inventors: James S. Marotta; Guy LaTorre; Christopher Batich, all of Gainesville, Fla.; Larry L. Hench, London, United Kingdom

[73] Assignees: University of Florida Research Foundation, Inc.; USBiomaterials, Inc., both of Gainesville, Fla.

[21] Appl. No.: 08/948,836

[22] Filed: Oct. 10, 1997

[51] Int. Cl.$^6$ .................................................. A61F 2/02
[52] U.S. Cl. .............................. 623/11; 623/66; 427/2.28
[58] Field of Search ................................. 623/11, 12, 66; 427/2.24, 2.28

[56] References Cited

U.S. PATENT DOCUMENTS

| | | |
|---|---|---|
| 4,131,597 | 12/1978 | Bliiethgen et al. . |
| 4,168,326 | 9/1979 | Broemer et al. . |
| 4,613,516 | 9/1986 | Kucheria et al. . |
| 4,652,459 | 3/1987 | Engelhardt . |
| 4,731,394 | 3/1988 | Vogel et al. . |
| 4,871,384 | 10/1989 | Kasuga . |
| 4,990,163 | 2/1991 | Ducheyne et al. . |
| 5,068,122 | 11/1991 | Kokabo et al. . |
| 5,380,298 | 1/1995 | Zabetakis et al. . |
| 5,480,438 | 1/1996 | Arima et al. . |
| 5,522,896 | 6/1996 | Prescott . |
| 5,604,976 | 2/1997 | Stobie et al. . |

OTHER PUBLICATIONS

Aoki, H., et al., *Medical Progress Tech.*, 12: 213–220, 1970.
Ducheyne, P., *J. Biomed Mater. Res.*, 19: 273–291, 1985.
Hench, L.L., *J. Am. Ceram. Soc.*, 74: 1487–1510, 1991.
Hench, L.L., *J. Biomed. Mater. Res. Symp.*, 2(1): 117–141, 1971.
Jansen, J.A. et al., *J. Mater. Sci. Mate. Med.*, 1: 192–197, 1990.
Jansen, J.A. et al., *J. Biomed. Mater. Res.*, 25: 1535–1545, 1991.
Klein, C.P.A.T. et al., *An Introduction to Bioceramics*, Eds. World Scientific, Singapore, 199–221, 1993.
Kokubo, T. et al., *J. Biomed. Mater. Res.*, 24: 721–734, 1990.
Luzar, M.A., *Perit. Dial. Int.*, 11: 333–340, 1991.
Hench, L.L., Wilson, J., *Handbook of Bioactive Ceramics*, CRC, 1: 235–244 and 283–302, 1990.
Yoshiyama, N., et al., *Perit. Dial. Int.*, 11(suppl. 1): 297, 1991.
Zabetakis, P.M., et al., *ASAIO J.*, 40, M896–M899, 1994.

*Primary Examiner*—Mickey Yu
*Assistant Examiner*—Dinh X. Nguyen
*Attorney, Agent, or Firm*—Burns, Doane, Swecker & Mathis, L.L.P.

[57] ABSTRACT

Percutaneous implants are disclosed including a portion implantable into a patient, a dermal bonding region capable of forming a bond between the implant and a dermal layer of the patient after the implantable portion is implanted into the patient, and the dermal bonding region including a substrate with a discontinuous coating of particulate bioactive glass wherein the average spacing between the particles of bioactive glass is predetermined and at least about 20 microns prior to implantation into the patient. Also disclosed are bioactive coatings including a substrate and fibers and/or particles of bioactive glass distributed on the substrate with a predetermined average interfiber distance of at least about 20 microns.

7 Claims, 4 Drawing Sheets

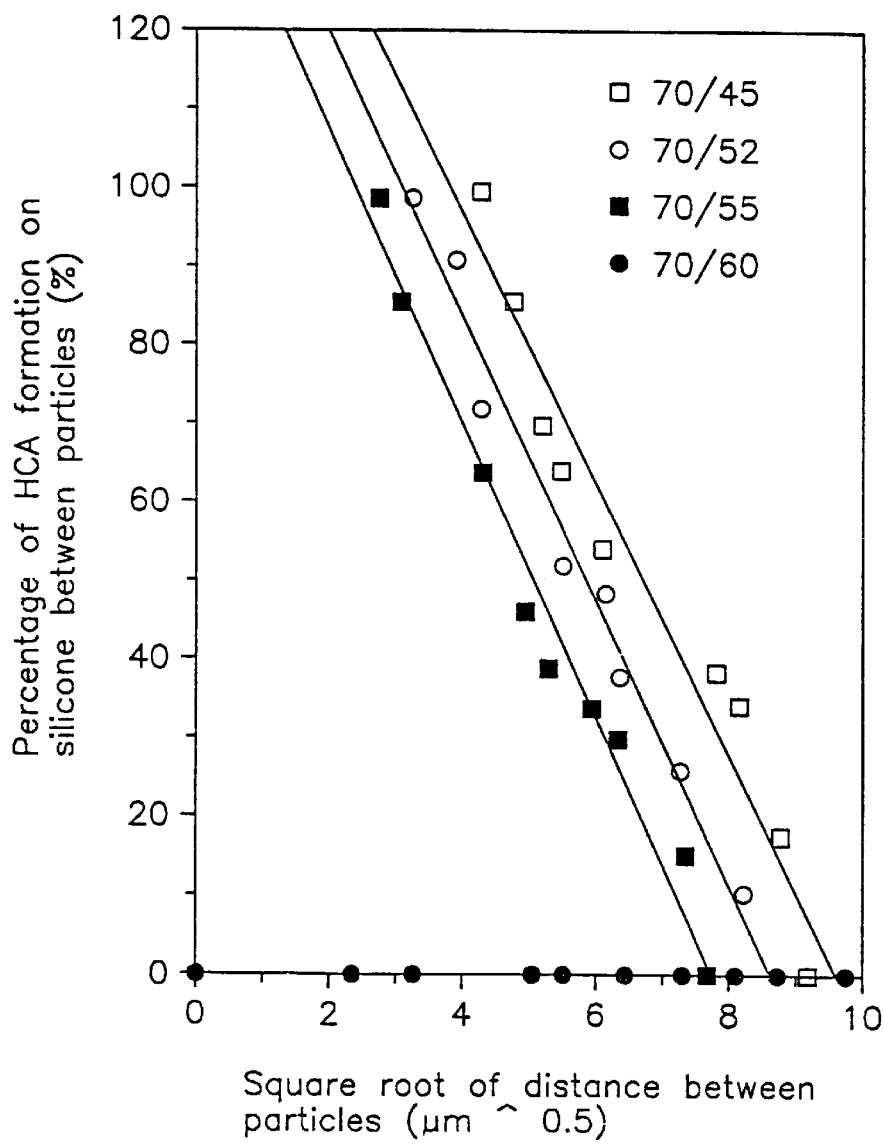
FIG. 4: Plot of the square root of the distance between particles (μm ^ 0.5) vs. the estimated percentage of HCA formation on the silicone between particles after 12 hours in SBF.

PERCUTANEOUS BIOFIXED MEDICAL IMPLANTS

FIELD OF THE INVENTION

This invention relates to percutaneous bioactive implants. More specifically, the present invention relates to percutaneous implants having specialized coatings for achieving superior bonding to dermal regions, thereby minimizing epithelial downgrowth and fibrous encapsulation.

BACKGROUND OF THE INVENTION

Elastomeric silicone polymers are widely used in the field of medicine. The most common type of silicone polymer, polydimethyl siloxane (PDMS), has generally been considered to be biologically inert when implanted in the body. However, the development of a fibrous tissue capsule around silicone implants continues to be a significant problem when this material is implanted for a long period of time. Capsule formation and subsequent capsular contracture can lead to pain, implant extrusion, erosion of surrounding tissue and ultimately implant failure.

One medical implant where this mode of failure is clearly evident is in percutaneous (through the skin) access devices. The lack of tissue bonding leads to the invasion of bacteria and subsequent infection. Earlier devices have lead to infection at the access site and the ultimate failure and removal of the implant.

The design of a percutaneous access device is one of the most challenging problems that faces the medical community today. One of the most common percutaneous devices used today is the peritoneal dialysis (PD) catheter, which consists of a catheter with fabric cuffs that is placed subcutaneous to anchor the device with scar tissue. Subcutaneous scar tissue forms early in the healing process around the cuffs and provides an anchor for the device at the exit-site. During a longer term, the epithelial tissue tunnels down around the catheter. This downgrowth provides access to bacteria and other pathogens that cause infection. These infections are the one barrier to greater use of these devices, Luzar, M. A., *Perit. Dial. Int.* 11, 333–340, 1991, and are caused by the lack of a tight seal around the catheter at the catheter-skin interface.

This need for improved percutaneous access has encouraged research efforts into both coating and design changes. Percutaneous implants have been tested that are anchored to either the cranium or tibia of animals, Jansen, J. A., et al., *J. Mater. Sci. Mater. Med.* 1, 192–197, 1990. The authors concluded that stabilization of a percutaneous implant was a requirement for a successful percutaneous passage. Realizing that there are many percutaneous access situations which can not be anchored to bone, this group tested an access device consisting of a 3 cm by 4 cm sintered titanium fiber mesh implanted subcutaneously and then attached to a Teflon percutaneous component, Jansen, J. A., et al., *J. Biomed. Mater. Res.* 25, 1535–1545, 1991. Fibrous tissue ingrowth of the mesh was intended to stabilize the implant, but early results with this implant showed that failure by tearing of the fiber mesh occurred in 30% of the implants.

One experimental device that has successfully reduced the amount of epidermal downgrowth in percutaneous implantation is made of sintered hydroxyapatite (HAP). HAP, $Ca_5(PO_4)_6OH$, a calcium phosphate mineral, is a major component of bone. This material has been used in medicine and dentistry for more than 20 years, Hench, L. L., *J. Am. Ceram. Soc.* 74, 1487–1510, 1991. A comparative study of these devices showed that the silicone devices had epidermal downgrowth that reached the bottom of the implant and a high rate of infection and extrusion of the implant after only 3 months. Devices made of HAP revealed limited epidermal downgrowth ($\geq 1$ mm) at 7 months and a mild infection at 17 months, Aoki, H., et al., *Med. Progress Tech.* 12, 213–220, 1987. In an additional animal PD study, dogs survived for 432 days on PD without exit-site infection, using an HAP percutaneous-access device/catheter, Yoshiyama, N., et al., *Perit. Dial. Int.* 11(Suppl 1), 297, 1991. The authors of this later study observed a "tight and sterile seal between the HAP device and skin tissue." These devices are brittle and require a silicone tube passing through their center, the junction between the tube and the device being a possible access for infection.

In 1969, Hench and colleagues discovered a certain range of glass compositions that could chemically bond to bones, Hench, L. L. et al., *J. Biomed. Mater. Res. Symp.* 2(1), 117–141, 1971. One such group of bioactive glasses, called Bioglass®, composed of $SiO_2O$, CaO and $P_2O_5$, is currently used in several medical applications, and is marketed under the trademark Bioglass® (a registered trademark of the University of Florida, currently licensed to USBiomaterials, Inc., Alachua, Fla.). Bioglass® is one of the few materials that does not produce a fibrous capsule when implanted in the body and certain Bioglass® compositions even develop an adherent bond to soft tissue, Wilson, J., Nolletti, D., *Handbook of Bioactive Ceramics Vol.* 1, CRC Press, Boca Raton, Fla., 283–302, 1990. Bioactive ceramic materials, like Bioglass®, are inherently brittle and can not be used in bulk applications where a flexible material is needed. Coating medical devices with a bioactive glass will allow for improved soft tissue adhesion without formation of an intervening fibrous capsule, stop or reduce the epithelia downgrowth, and create a better seal that prevents bacterial access and infection.

Some of the earliest applications of bioactive glass coatings were on metal femoral implants. These coatings were either dip coated from molten glass or fired onto the metal with an enamel frit, Ducheyne, P., *J Biomed Mater Res* 19:273–291, 1985. Several references of the art relate to coating bioactive glass on various metal substrates, e.g., U.S. Pat. Nos. 5,480,438; 4,990,163; 4,613,516; 4,652,459; and 4,168,326.

Bioactive glasses have also been used as filler materials in bone cements, e.g. methacrylates and epoxies, as taught in U.S. Pat. Nos. 4,731,394 and 4,131,597. While certainly useful, application of these materials is limited because they are brittle, thermoset plastics, which do not have the elastomeric properties of silicone polymers used extensively in modern surgery. Precipitation of calcium phosphate and hydroxyapatite films on a substrate is known in the art, e.g. see U.S. Pat. Nos. 5,068,122 and 4,871,384. Experience has shown that these brittle films will not adhere to or spread evenly over, the hydrophobic silicone surface and will flake off after repeated flexure of the elastomer.

One technique to coat the entire implant is to use a pulsed laser deposition as described in U.S. Pat. No. 5,380,298 and published in Zabetakis, P. M., et al. ASAIO J. 40, M896–M899, 1994. A thin amorphous film of hydroxyapatite was applied to the surface of silicone tubing. The film measured between 0.5 to 1 microns in thickness and could be applied to a selected area. The coating was described as continuous. The coating failed insofar as it formed cracks when the tubing was bent. It is unclear how this cracked, amorphous and extremely thin coating would react in a percutaneous application. In addition, it is unclear how this coating process would effect the nature of bioactive glasses.

Studies have shown that high temperature processes such as these can greatly alter the chemical and physical nature of bioactive glasses, thus reducing their effectiveness, Klein et al., An Introduction to Bioceramics, Hench, L. L., Wilson, J. Eds. World Scientific, Singapore, 199–221, 1993.

U.S. Pat. No. 5,522,896 ("the '896 patent") discloses a non-percutaneous prosthesis, reconstructive sheeting and composite material which exhibit tissue adhesion and biocompatability, moldability, trimability and flexibility. Experiment No. 7 of the '896 patent describes coating silicone adhesive onto a breast prosthesis. Greater than 200 mesh hydroxyapatite was spread onto a flat surface. The adhesive-coated surface was pressed onto the hydroxyapatite particles, and hydroxyapatite particles smaller than 300 mesh were sprinkled onto the coated surface to fill in the voids between the larger hydroxyapatite particles. The non-percutaneous prosthesis comprises a biocompatible composite material which is made of an elastomeric material and bio-active ceramic or glass particles.

SUMMARY OF THE INVENTION

The present invention concerns a percutaneous implant including a portion implantable into a patient, a dermal bonding region capable of forming a bond between the implant and a dermal layer of the patient after the implantable portion is implanted into the patient, and the dermal bonding region including a substrate with a discontinuous coating of particulate bioactive glass wherein the average spacing between the particles of bioactive glass is predetermined and averages at least about 20 microns prior to implantation into the patient. The present invention also relates to coatings including particles of bioactive glass dispersed at predetermined distances. The present invention further relates to methods of preparing percutaneous implants and coatings.

BRIEF DESCRIPTION OF THE DRAWINGS

FIG. 4 is a plot of the square root of the distance between particles vs. the estimated percentage of HCA formation on the silicone between particles after 12 hours in SBF.

DETAILED DESCRIPTION OF THE INVENTION

Figure 1:
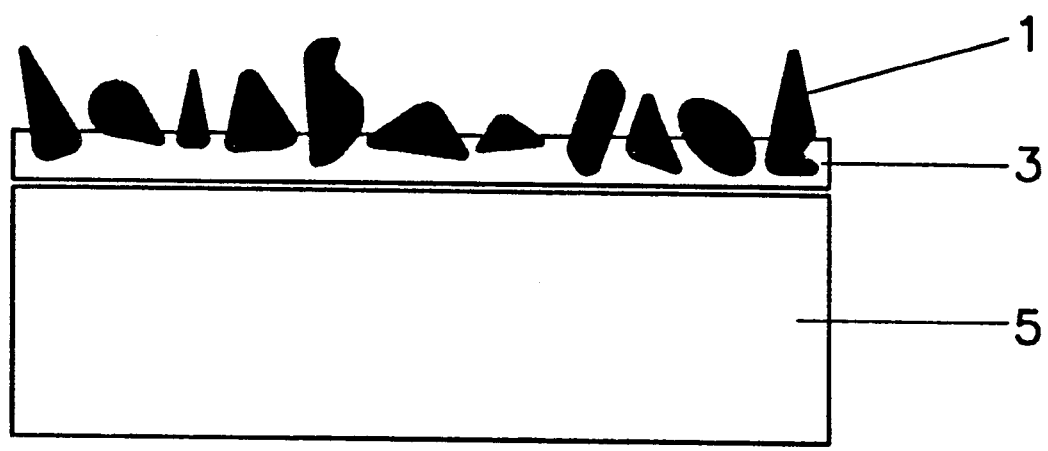
FIG. 1 is a schematic illustration of an example of a percutaneous implant in accordance with the present invention. (1) represents the particulate bioactive glass, (3) represents a silicone polymer substrate and (5) represents an implantable medical device.

Percutaneous implants and coatings have now been discovered which combine the elastomeric properties of a substrate with the biologic properties of a bioactive glass. The coating of existing medical devices with this material substantially improves soft tissue response at the interface and may be used on a variety of medical devices where soft tissue must interact directly with the medical device for an extended period. The result is an implant that has the bulk mechanical properties of a flexible elastomer, and the bioactive properties of the glass or ceramic, which enables the composite to bond to soft tissue.

The present invention concerns a percutaneous implant including a portion implantable into a patient, a dermal bonding region capable of forming a bond between the implant and a dermal layer of the patient after the implantable portion is implanted into the patient, and the dermal bonding region including a substrate with a discontinuous coating of particulate bioactive glass wherein the average spacing between the particles of bioactive glass is predetermined and at least about 20 microns prior to implantation into the patient. The present invention also relates to coatings including particles of bioactive glass dispersed at predetermined distances. The present invention further relates to methods of preparing percutaneous implants and coatings.

The present invention overcomes many of the disadvantages associated with the prior art. The bioactive component of the present invention includes a discontinuous layer of particles or fibers on the outer surface of a substrate. Interference with the flexible nature of the substrate is minimized and cracking of the bioactive layer is avoided because the particles or fibers are discrete and are free to flex with the underlying substrate. In contrast, implants and coatings such as those described in U.S. Pat. No. 5,380,298 tend to crack (See column 10, lines 39–45). It has unexpectedly been found that compositions in accordance with the present invention have predetermined spacings between particles or fibers of bioactive glass and avoid such disadvantages. Specifically, it was unexpected that a discontinuous layer of bioactive particulate glass could induce apatite mineralization on and between particles, which could establish acceptable bonding in the dermal region in view of the typically non-bioactive nature of the substrate or implant surface on which the discontinuous layer is adhered or embedded.

Examples of such medical devices include, but are not limited to, those having some type of connective interface between the body of a mammal, in particular a human, and the outside environment, e.g., as percutaneous drain tubes, artificial ear implants, electrical connections, pace-maker wires, cannulas, and subcutaneous peritoneal dialysis catheters, etc. A material that has improved soft tissue bonding could be adapted as a coating on these medical devices.

Yet another aspect of the present invention is a method of preparing the bioactive silicone formulation of the first aspect which involves blending finely divided units of bioactive glass into an uncured elastomeric, silicone polymer followed by curing the silicone polymer to achieve an appropriate surface particle density. This aspect also includes a method for fabricating medical devices from the formulation of the first aspect.

As used herein the term "biologically active glass", also known as "bioactive glass" means a material, either glass or glass-ceramic, that is known to bond with tissue when implanted in the body or form HCA when implanted into a patient. The term "percutaneous access" refers to a method or apparatus for connecting the outside environment, through the skin or other soft tissue, with the inside of the body. The term "curing" or "cure" means a non-reversible chemical reaction of polymers to form a tough elastomeric material.

The average spacing between particles of bioactive glass is predetermined and can vary depending upon the size of the particles. Preferably, the spacing between the particles is at least 20 about microns.

The present invention unexpectedly provides for a flexible percutaneous implant that achieves a level of bioactivity and direct tissue bonding to provide an adequate seal in the dermal bonding region of the implant to minimize infection and extrusion of the device. As used herein, the term (dermal bonding region) is intended to mean any region of the percutaneous implant that comes in contact with and bonds to a patients dermal layer. For the purposes of the present invention the term (dermal layer) includes any flexible structure such as skin, muscle, ear drum and fatty tissue. The present invention provides a unique combination of bioactive surface layer while maintaining adequate flexibility i.e., a range of particle spacings which provides for HCA formation and adequate tissue bonding while maintain adequate flexibility of the construct. Conventional implants include monolithic forms of bioactive glasses which are inflexible and lead to infection, tearing, and extrusion of the implant if used in a percutaneous applications because no adequate seal is formed at the junction of the implant and the dermal layer of the patient.

The surface coating of the present invention has been shown to produce a crystalline hydroxy carbonate apatite layer on both the Bioglass® particle and the silicone surface between particles, when placed in simulated body fluid (SBF, a solution used to test bioactivity first described by Kokubo, T., et al., *J. Biomed. Mater. Res.* 24, 721–734, 1990) at 37° C. for a period of 10 days. The formation of a hydroxy carbonate apatite (HCA) layer at the surface of a bioactive glass is essential for bonding to bone or soft tissue.

The bioactivity of coated samples produced using the technique described above, was tested in vitro by placing them in a solution of SBF at 37° C. for 20 hours and 10 days. The surface of reacted samples was analyzed using Fourier Transform Infrared (FTIR) Spectroscopy. Comparison of the Si—O stretching, P—O stretching, and P—O bending peaks confirmed the formation of a crystalline HCA layer on the surface of the coated silicone samples. Surface analysis using low voltage scanning electron microscopy (SEM) showed an HCA layer on both the Bioglass® particles and on the silicone between the particles.

A further embodiment of the present invention is a bioactive silicone tape made in a similar manner to that above. The silicone is cast into a thin sheet and the glass applied to one side of the sheet. This sheet then has an adhesive applied to the other side. Pieces of this tape could be applied to an area on an existing device where bioactive reactions are required.

In accordance with several embodiments of the present invention, it has been found that it is preferable to include bioactive particles of different size ranges. For example, it is preferable in some circumstances to use a combination of large and small particles. The use of large particles is beneficial because these particles continue to leach ions needed for HCA formation days or weeks after implantation. However, the use of small particles lend themselves to greater flexibility of the construct. Small particles, in the context of the present invention, are those that leach substantially all of their ions within about 12 to 24 hours of implantation. Larger particles are those that take days or weeks to exhaust their supply of ions.

EXAMPLE 1

Controlled Coating

Using a micropipeter, 0.15 mL of a 10 weigh % silicone/hexane solution was applied to one end of a square of silicone sheeting, and spread using a glass slide. Once the hexane evaporated, a piece of 70 $\mu$m Specta/Mesh® (Lot#00450, Spectrum Medical Industries, Inc., Houston, Tex.) was gently applied on top of the uncured silicone layer. Bioactive glass powder (45s5 Bioglass®, 125–53 $\mu$m diameter) was spread onto this masked surface. Once the glass powder had filled all of the pores in the mesh, the excess glass was gently blown off using compressed dry air. The nylon mesh was removed, leaving a pattern of single glass particles. The sample was placed in a vacuum oven at 10 Torr and 70° C. for 24 hours.

Figure 2:
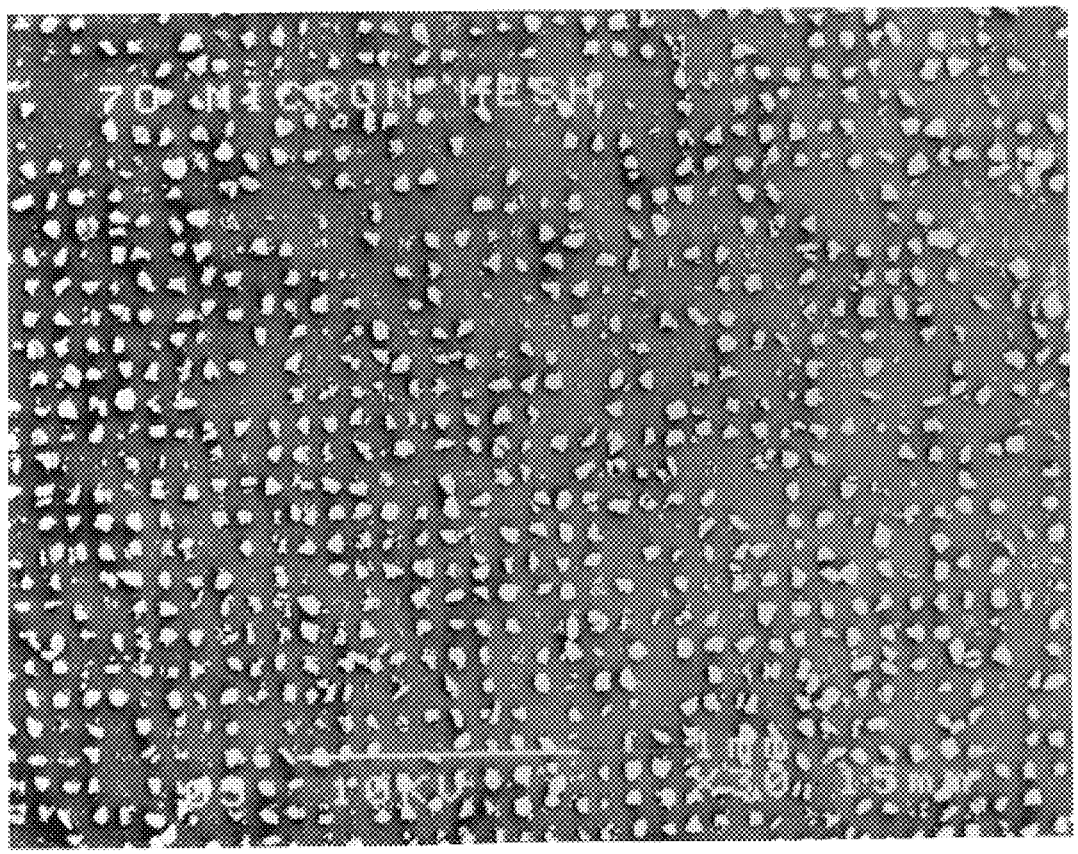
FIG. 2 is a scanning electron microscope (SEM) micrograph of a sample made using a 70 mesh filtration mask. Note the glass particles on the surface of predetermined spacing.
Figure 3:
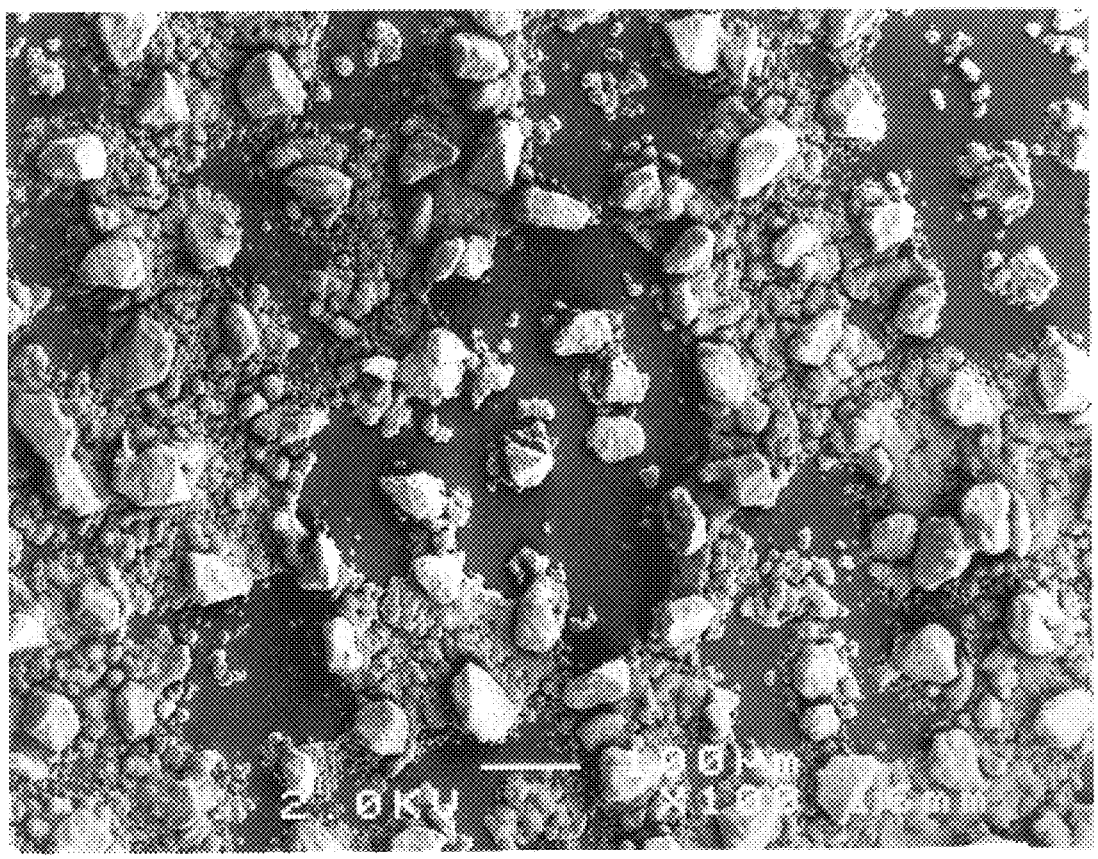
FIG. 3 is a SEM of a 70 mesh spaced sample reacted in simulated body fluid (SBF) for 3 days at 37° C. An HCA layer can be seen between particles that are 100 microns apart. A circle of HCA can be seen on the border of an open area where a missing particle has caused a lack of HCA precipitation on the silicone surface.

The surface produced using this method had single bioactive glass particles evenly spaced apart in rows 70 $\mu$m apart (see FIG. 2). Initial bioactivity testing included single samples tested at 1, 2, and 3 days in SBF at 37° C. SEM images of the surface of these samples revealed HCA growth both on the bioactive glass particles and the silicone between them (see FIG. 3). This result was observed if the particles were less than 100 $\mu$m apart. When individual particles were missing from the pattern, the HCA layer was not present on the silicone between the particles.

The unexpected formation of this HCA layer between the bioactive glass particles was found to be a function of the glass composition, particle size and the distance between particles (as shown in FIG. 4). A linear curve fit is plotted along with each of these compositions and gave the best $r^2$ value (shown in table 1). Samples of 70/60 glass had no HCA formation on the glass particles themselves or on the silicone between them at any distance. The close linear correlation of a plot of HCA formation with the square root of the distance suggest that this reaction is a diffusion controlled process. The linear curve fits for all 3 glass compositions have similar decreasing slopes with distances suggesting that the HCA formation is similar in each case and that the concentration varies with distance. The only difference is how far apart the 100% coverage extends for each composition suggesting similar diffusion coefficients with an offset due to the initial glass concentration.

TABLE 1

| Sample Name | $SiO_2$ (mole %) | $Na_2O$ (mole %) | CaO (mole %) | $P_2O_5$ (mole %) | Ca/P ratio |
|---|---|---|---|---|---|
| 70/45 | 46.1 | 24.4 | 26.9 | 2.6 | 5 |
| 70/52 | 52.1 | 21.5 | 23.8 | 2.6 | 4.6 |
| 70/55 | 55.1 | 20.1 | 22.2 | 2.6 | 4.3 |
| 70.60 | 60.1 | 17.7 | 19.6 | 2.6 | 3.8 |

Several combinations of uncured silicone thickness, mesh size and particle size led to this coating method. If too thin a layer of uncured silicone was used, then the particles on the surface would dissolve away into the solution during reaction. If too large a mesh size were used, then the sample would have small clusters of particles on the surface.

EXAMPLE 2

Varied Amounts of Bioactive Glass

Six squares of silicone elastomer sheeting were soaked in hexane for 2 hours. Using a glass pipet, 1 mL of a 10 weight % solution of silicone/hexane was applied evenly to the surface of each silicone square and the hexane allowed to evaporate. This produced a thin layer of uncured silicone on the surface of each square. A weighted amount (0.0, 0.1, 0.2, 0.3, 0.4 and 0.5 g) of bioactive glass (45s5 Bioglass®, 125–53 $\mu$m diameter) powder was evenly applied to each square using a "salt shaker"-like device. Each square was then placed between two Teflon sheets and pressed in a heated Carver press at 150° C. to 5000 psi for 1 hour.

After samples were reacted in SBF for 10 minutes and 1, 2, 6, and 20 hours, the reacted surface of each square was analyzed using Fourier transform infrared (FTIR) spectroscopy. Results showed that if no bioactive glass particles were exposed at the surface of the composite coating, then there was no reaction at the surface. Samples with 0.0, 0.1 and 0.2 g of bioactive glass powder added showed no exposed particles with SEM and no reaction in the SBF solution. Samples with 0.3, 0.4, and 0.5 g of powder added showed exposed particles and reacted in SBF to form a hydroxy carbonate apatite (HCA) layer. The formation of this HCA layer is essential for bioactivity of the coating.

EXAMPLE 3

Coating a Percutaneous Dialysis Catheter

Experimental dialysis catheters (Baxter Healthcare, McGraw Park, Ill.) were coated with the bioactive composite coating as described in Example 1. These catheters consisted of a single silicone tube (outer diameter 5.1 mm) with 2 Dacron velour cuffs attached. Dip coating of the entire catheter in a silicone/hexane solution was performed. The catheter was then allowed to dry and was rolled in an excess of Bioactive glass powder (45s5 Bioglass®, 125–53 μm diameter, Lot# VIOX). The catheter was then cured in an oven at 70° C. for 24 hours.

SEM analysis of the surface revealed that not only was the outside of the silicone tube coated with the bioactive composite coating, but the individual fibers of the Dacron velour were also coated with bioactive glass particles. This may improve the bioactive properties of the velour cuff.

What is claimed is:

1. A percutaneous implant comprising:

a portion implantable into a patient providing percutaneous access thereto, a dermal bonding region capable of forming a bond between said implant and a dermal layer of the patient after said implantable portion is implanted into the patient, and;

said dermal bonding region comprising a substrate with a discontinuous coating of particulate bioactive glass wherein the average spacing between the particles of bioactive glass is predetermined and average at least about 20 microns prior to implant into the patient.

2. The bioactive percutaneous implant of claim 1, wherein said particles have an average spacing of at least about 40 microns.

3. The bioactive percutaneous implant of claim 1, wherein said particles have an average spacing of at least about 60 microns.

4. The implant of claim 1, wherein the bioactive glass is a glass or glass-ceramic made from 30–95% $SiO_2$, 0–35% CaO, 0–35% $Na_2O$, and 0–15% $P_2O_5$.

5. The composite of claim 1, wherein said bioactive glass is melt-derived or sol-gel derived.

6. The bioactive percutaneous implant of claim 1, wherein said particles have an average spacing of at least about 150 microns.

7. The bioactive percutaneous implant of claim 1, wherein said particles have an average spacing of at least about 200 microns.

* * * * *